United States Patent [19]

Bernstein

[11] Patent Number: 4,588,590

[45] Date of Patent: May 13, 1986

[54] METHOD OF TREATING KERATOSIS AND COMPOSITIONS USEFUL THEREFOR

[75] Inventor: Joel E. Bernstein, Deerfield, Ill.

[73] Assignee: Jaye-Boern Laboratories, Inc., Northbrook, Ill.

[21] Appl. No.: 572,899

[22] Filed: Jan. 23, 1984

Related U.S. Application Data

[63] Continuation-in-part of Ser. No. 332,676, Dec. 21, 1981, abandoned.

[51] Int. Cl.[4] .................... A61K 35/78; A61K 7/04; A61K 31/60; A61K 31/19

[52] U.S. Cl. .................... 424/195.1; 424/61; 514/159; 514/474; 514/557; 514/563

[58] Field of Search .................... 424/145, 61, 230, 317, 424/195.1; 514/159, 474, 557, 563

[56] References Cited

U.S. PATENT DOCUMENTS 2,261,623 11/1941 Hucks .................... 424/61
2,799,613 7/1957 Blodorn .................... 424/61
3,984,566 10/1976 Van Scott et al. .................... 424/283
4,302,442 11/1981 Socci et al. .................... 424/61
4,380,549 4/1983 Van Scott et al. .................... 424/317

OTHER PUBLICATIONS

*Handbook of Non-Prescription Drugs*, pp. 378–379 (1977).
*Fed. Register*, 45(194):65612, 65613 (1980, Oct.).
*Martindale, The Extra Pharm.*, (1982 edition).
*AMA Drug Evaluations*, 5th ed. p. 1361.
*Handbook of Non-Prescrip. Drugs*, 6th ed., p. 436.

*Primary Examiner*—Albert T. Meyers
*Assistant Examiner*—Freda Abramson
*Attorney, Agent, or Firm*—Ronald A. Sandler; Jerry A. Schulman; Timothy T. Patula

[57] ABSTRACT

The present invention includes an improved method of treating keratosis comprising periodically applying to the affected area a nail polish composition containing an effective amount of at least one corrosive agent for relieving the keratosis; also nail polish compositions are disclosed for use in the method.

11 Claims, No Drawings

METHOD OF TREATING KERATOSIS AND COMPOSITIONS USEFUL THEREFOR

BACKGROUND OF THE INVENTION

This is a continuation-in-part of application Ser. No. 332,676, filed Dec. 21, 1981, since abandoned.

This invention generally relates to an improved method of treating keratosis and is particularly directed to novel nail polish compositions for use in such improved method.

Keratosis is generally used to describe any disease of the skin characterized by an overgrowth of the epithelium. In particular, these diseases include what are commonly referred to as warts, corns and calluses. Warts are small intraepidermal growths of the skin caused by human papilloma virus and appear in children and young adults on the hands, face and feet. Corns are sharply demarcated hyperkeratotic lesions with a central core which are observed almost exclusively on the feet. Calluses are also hyperkeratotic lesions but have no central core and have a more diffuse outline. Calluses appear on the feet and hands where they may cause pain and discomfort.

Treatment of keratosis includes the use of drugs with sufficient corrosive activity so as to cause peeling of the hyperkeratotic lesion. Topical corrosive agents used in the treatment of keratosis incude ascorbic acid, glacial acetic acid, lactic acid, salicylic acid, trichloroacetic acid, calcium pantothenate, zinc chloride, and podophyllum resin.

The corrosive agents are generally formulated in flexible collodion vehicles or volatile solvents such as ether or alcohol. Although the collodion vehicles and solvents used in the prior art moderately reduce moisture exchange between the skin and the environment, they are not completely occlusive. It is desirable to form a completely occlusive film over the keratotic area to prevent moisture exchange between the skin and the environment, and thus increase the activity of the corrosive agent. Furthermore, the collodion vehicles and solvents used heretofore deteriorate rapidly, requiring several applications per day in order to expose the keratotic condition to the corrosive agent for a sufficient length of time.

The use of nail polish as a vehicle for applying topical steriods to nails is disclosed in U.S. patent application Ser. No. 28,092, for "A Method for Treating Psoriasis of the Nails and Composition". The nail polish compositions disclosed therein induce a soothing, anti-inflammatory effect on the nails affected by psoriasis. By contrast, the nail polish compositions of the present invention produce an occlusion having a corrosive, inflammatory and irritating effect on the skin.

SUMMARY OF THE DISCLOSURE

It is an object of the invention to provide an improved method of treating keratosis with a nail polish composition which reduces the moisture exchange between the skin and the environment.

It is a further object of the invention to provde a nail polish composition which increases the activity of the corrosive agent incorporated in the composition.

A still further object of the invention is to provide a nail polish composition which covers the area of the skin affected by keratosis for more than a day, before deterioration of the composition requires reapplication.

Another object of the invention is to provide a method for relieving keratosis which is easy, convenient, and simple for children or adults to use.

Still another object of the invention is to provide a nail polish composition for relieving keratosis which is relatively inexpensive and generally affordable by the public.

Keratosis is treated by periodically applying to the affected area a nail polish composition containing an effective amount of at least one corrosive agent for relieving the keratosis.

For a better understanding of the present invention, together with other and further objects thereof, references are made to the following description, taken in connection with the accompanying examples. The scope of the invention will be pointed out in the appended claims.

DETAILED DESCRIPTION OF THE PREFERRED EMBODIMENTS

In the practice of the present invention, at least one corrosive agent is incorporated into a nail polish vehicle which is applied over the area affected by keratosis. The application of the nail polish composition is a simple covering of the affected area by brushing, smearing, or painting. The composition dries quickly to form a fairly durable cover.

The present invention contemplates the use of a corrosive agent which gradually wears away the keratotic lesion by chemical action. A suitable corrosive agent is identified by its corrosive, inflammatory, and irritating action on the affected area of the skin. The corrosive agent must also be non-toxic and otherwise pharmaceutically acceptable. Exemplary corrosive agents include acids, in particular, those carboxylic acids which are pharmaceutically acceptable. In particular, the following chemicals are known corrosive agents and are preferred for use in the invention: ascorbic acid, glacial acetic acid, lactic acid, salicylic acid, trichloroacetic acid, calcium pantothenate, zinc chloride, and podophyllum resin. The present invention contemplate the use of other known corrosive agents as well.

The corrosive agent incorporated in the nail polish composition is present in an amount effective to relieve the keratotic condition with periodic application. More than one corrosive agent may be included in the nail polish composition. Preferably, each corrosive agent is present in an amount between about 5% and 40% of the total weight of the composition. A more preferred range for each corrosive agent in the composition is an amount between about 5% and 20% of the total weight.

The present invention contemplates the use of any commercial nail polish, colored or clear, as a vehicle for the corrosive agent. It is critical, however, that the selected nail polish form an occlusion over the affected area when dry. Although nail polishes manufactured under the trade names Revlon and Cutex are used in the examples below, these nail polishes are for illustrative purposes only and are not intended as a limitation.

Having described the invention in general terms, the following examples are set forth to more fully illustrate the preferred embodiments of the invention. These examples, however, are not meant to be limiting. It is possible to produce still other embodiments without departing from the inventive concept herein disclosed. Such embodiments are within the ability of one skilled in the art.

EXAMPLE 1

A nail polish composition useful in treating keratosis was prepared by mixing salicylic acid with Revlon clear nail polish in the amount of 1% by total weight and painting a wart on the foot of an 11 year old boy every 48 hours for 3 weeks with the composition. Unexpectedly, all signs of the wart disappeared with this treatment regimen.

EXAMPLE 2

A nail polish composition was prepared by mixing salicylic acid in Cutex clear nail polish in the amount of 5% by weight. The composition was applied to 5 warts on the hands of a 7 year old girl once daily for 2 weeks. Once again, the warts flattened and disappeared over this period with only one wart requiring freezing of the base.

EXAMPLE 3

A nail polish composition was prepared by mixing salicylic acid in Revlon clear nail polish in the amount of 20% by weight and the resulting composition was applied to a corn on the lateral surface of the left foot of a 37 year old woman. Unanticipated results were obtained. With similar applications made every 48 hours for 2 weeks, the corn totally disappeared.

EXAMPLE 4

A nail polish composition was prepared by mixing lactic acid into Revlon clear nail polish in the amount of 10% by weight and the resulting composition was applied once daily to a wart one cm in diameter on the right hand of a 10 year old boy. A wart of the same size on the left hand was treated similarly with a daily application of a second nail polish composition which incorporated by weight 16% lactic acid and 16% salicylic acid in Revlon clear nail polish. After two weeks of treatment, the wart on the right hand disappeared and although the wart on the left hand nearly disappeared, some traces of the wart still remained which required additional treatment before disappearing completely.

EXAMPLE 5

A nail polish composition was prepared by mixing lactic acid in Cutex clear nail polish in the amount of 5% by weight and the resulting composition was applied 3 times weekly to a callus on the sole of the foot of a 38 year old male. Unforeseen, the callus disappeared within 10 days.

EXAMPLE 6

A nail polish composition was prepared by mixing glacial acetic acid in Revlon clear nail polish in the amount of 5% by weight and the resulting composition was applied once daily to 8 warts on the hands and elbows of a 24 year old female. Wholly unexpected results were obtained. Within 3 weeks, no trace of the warts remained.

EXAMPLE 7

A nail polish composition was prepared by incorporating by weight 10% lactic acid and 10% salicylic acid in Revlon clear nail polish and the resulting composition was applied every other day to a large plantars wart on the sole of an 11 year old boy. After 21 days of such therapy, the wart was nearly disappeared. After freezing the base, the plantars wart never recurred.

EXAMPLE 8

A nail polish composition was prepared by mixing 15% lactic and 15% glacial acetic acid by weight in Revlon clear nail polish. The composition was applied once daily to calluses on the palms of a 38 year old man. After 1 week of such treatment the calluses disappeared.

EXAMPLE 9

A nail polish composition was prepared by mixing 5% salicylic acid, 5% lactic acid and 5% glacial acetic acid by weight in Cutex clear nail polish and the resulting composition was applied once every 48 to 72 hours to a corn on the big toe of a 30 year old female. Unexpectedly, the corn disappeared after 2 weeks of treatment.

EXAMPLE 10

A nail polish composition was prepared by mixing 20% lactic acid and 20% glacial acetic acid by weight in Revlon clear nail polish and the resulting composition was applied once every 3 days to a wart on the dorsum of the right hand of a 13 year old gir. Although the skin surrounding the wart became mildly irritated, the wart disappeared within 2 weeks of treatment.

As demonstrated by these examples, this invention provides an improved method and composition for treating keratosis. The occlusion formed by the nail polish composition over the affected area reduces the moisture exchange between the skin and the environment. The durability of the nail polish composition covering the affected area allows for prolonged contact with the corrosive agent. For these reasons, the activity of the corrosive agent on the keratotic condition is increased, with fewer applications of the corrosive agent.

These examples also show that the present invention provides a method for relieving keratosis which is relatively painless, easy and convenient for both children and adults to use because of it simplicity. Furthermore, the invention is relatively inexpensive and would be affordable by the general public.

A small clinical study performed by Applicant compared the efficacy of varying concentrations of salicylic acid in a carrier for the purpose of treating warts. The results were as follows:

| Concentration of Salicylic Acid | No. of Warts Treated | % Cured or Improved |
|---|---|---|
| 1% | 5 | 20% |
| 5% | 4 | 75% |
| 17% | 5 | 80% |
| Carrier Only | 5 | 20% |

Thus, preferred results have been achieved through use of keratolytic substances of the types discussed hereinabove in amounts ranging from about 5% to about 20% by weight with respect to the carrier.

While there has been described what is at present considered to be the preferred embodiments of the invention, it will be obvious to those skilled in the art that various changes and modifications may be made therein, without departing from the invention and that it is, therefore, the intent of the appended claims to cover all such changes and modifications as fall within the true spirit and scope of the invention.

I claim:

1. A method of treating warts, corns, and calluses comprising periodically applying to the affected area a nail polish composition containing an effective amount of at least one non-toxic and pharmaceutically acceptable corrosive agent sufficient to cause peeling of the wart, corn, or callus for relieving said warts, corns, or calluses.

2. A method as defined in claim 1, wherein each said corrosive agent is a pharmaceutically acceptable acid.

3. A method as defined in claim 1, wherein each said corrosive agent is a pharmaceutically acceptable carboxylic acid.

4. A method as defined in claim 1, wherein each said corrosive agent is selected from the group consisting of salicylic acid, lactic acid, glacial acetic acid, ascorbic acid, calcium pantothenate, podophyllum resin, and trichloroacetic acid.

5. A method as defined in claim 1, wherein the total conentration of said corrosive agent or agents is an amount between about at least 5% and 40% by weight.

6. A nail polish composition for relieving warts, corns and calluses comprising a nail polish vehicle containing an effective amount of at least one non-toxic and pharmaceutically acceptable corrosive agent, in a concentration of at least 5% by weight, sufficient to cause peeling of said warts, corns, and calluses.

7. A nail polish composition as defined in claim 6, wherein each said corrosive agent is a pharmaceutically acceptable acid.

8. A nail polish composition as defined in claim 6, wherein each said corrosive agent is a pharmaceutically acceptable carboxylic acid.

9. A nail polish composition as defined in claim 6, wherein each said corrosive agent is selected from the group consisting of salicylic acid, lactic acid, glacial acetic acid, ascorbic acid, calcium pantothenate, podophyllum resin, and trichloroacetic acid.

10. A nail polish composition as defined in claim 6, wherein the total concentration of said corrosive agent or agents is an amount between about at least 5% and 40% by weight.

11. A nail polish composition as defined in claim 6, wherein the total concentration of said corrosive agent or agents is an amount between about at least 5% and 20% by weight.

* * * * *